United States Patent [19]
Jewett et al.

[11] Patent Number: 6,110,292
[45] Date of Patent: Aug. 29, 2000

[54] OSCILLATING LIQUID JET WASHING SYSTEM

[75] Inventors: Warren R. Jewett, 125 Palace Green, Cary, N.C. 27511; Tadeusz M. Drzewiecki, Rockville, Md.

[73] Assignees: Warren R. Jewett, Cary; Richard L. Bird, Raleigh, both of N.C.

[21] Appl. No.: 08/909,503

[22] Filed: Aug. 12, 1997

[51] Int. Cl.[7] ........................................... B08B 3/10
[52] U.S. Cl. ............................ 134/1; 134/18; 134/34; 134/184; 239/589.1; 137/803; 604/289; 128/DIG. 10
[58] Field of Search ......................... 134/64 R, 122 R, 134/44, 47, 52, 184, 1, 21, 26, 34, 199, 18, 56 R; 239/589.1; 137/803; 604/289; 128/DIG. 10

[56] References Cited

U.S. PATENT DOCUMENTS

| | | |
|---|---|---|
| Re. 33,448 | 11/1990 | Bauer . |
| Re. 33,605 | 6/1991 | Bauer . |
| 3,220,424 | 11/1965 | Nelson ........................................ 134/47 |
| 3,507,275 | 4/1970 | Walker . |
| 3,537,444 | 11/1970 | Gatn et al. ........................ 128/DIG. 10 |
| 3,563,462 | 2/1971 | Bauer . |
| 3,699,984 | 10/1972 | Davis ........................................ 134/199 |
| 3,757,806 | 9/1973 | Bhaskar et al. .......................... 134/199 |
| 3,770,200 | 11/1973 | Bauer et al. . |
| 3,918,987 | 11/1975 | Kopfer ...................................... 134/199 |
| 3,992,730 | 11/1976 | Davis . |
| 4,020,856 | 5/1977 | Masterson . |
| 4,184,636 | 1/1980 | Bauer . |
| 4,219,367 | 8/1980 | Cary, Jr. et al. ......................... 134/199 |
| 4,295,233 | 10/1981 | Hinkel et al. . |
| 4,402,331 | 9/1983 | Taldo et al. .............................. 134/199 |
| 4,670,010 | 6/1987 | Dragone . |
| 4,688,585 | 8/1987 | Vetter ..................................... 134/56 R |
| 4,803,979 | 2/1989 | Fischer . |
| 4,817,651 | 4/1989 | Crisp et al. .............................. 134/199 |
| 4,925,495 | 5/1990 | Crisp et al. ............................. 134/56 R |
| 4,942,631 | 7/1990 | Rosa . |
| 5,056,554 | 10/1991 | White . |
| 5,074,322 | 12/1991 | Jaw ....................................... 134/56 R |
| 5,193,563 | 3/1993 | Melech .................................... 134/199 |
| 5,265,628 | 11/1993 | Sage et al. ............................ 134/104.1 |
| 5,522,411 | 6/1996 | Johnson .................................... 134/44 |
| 5,727,579 | 3/1998 | Chardack ................................. 134/113 |

OTHER PUBLICATIONS

A New Method of Presurgical Hand Cleansing, vol. 33, No. 2, pp. 162–167.
Anatomy and Physiology, Chap. 4, pp. 56–63.

*Primary Examiner*—Frankie L. Stinson
*Attorney, Agent, or Firm*—Pitney, Hardin, Kipp & Szuch, LLP

[57] ABSTRACT

Fluidic oscillators are used to apply pulsatile sweeping streams of a liquid, preferably a cleansing solution, to selected areas of epidermis in a manner consistent with the resonant characteristics of the epidermis. The device thereby cleanses the skin, pores, and folds of microorganisms.

40 Claims, 8 Drawing Sheets

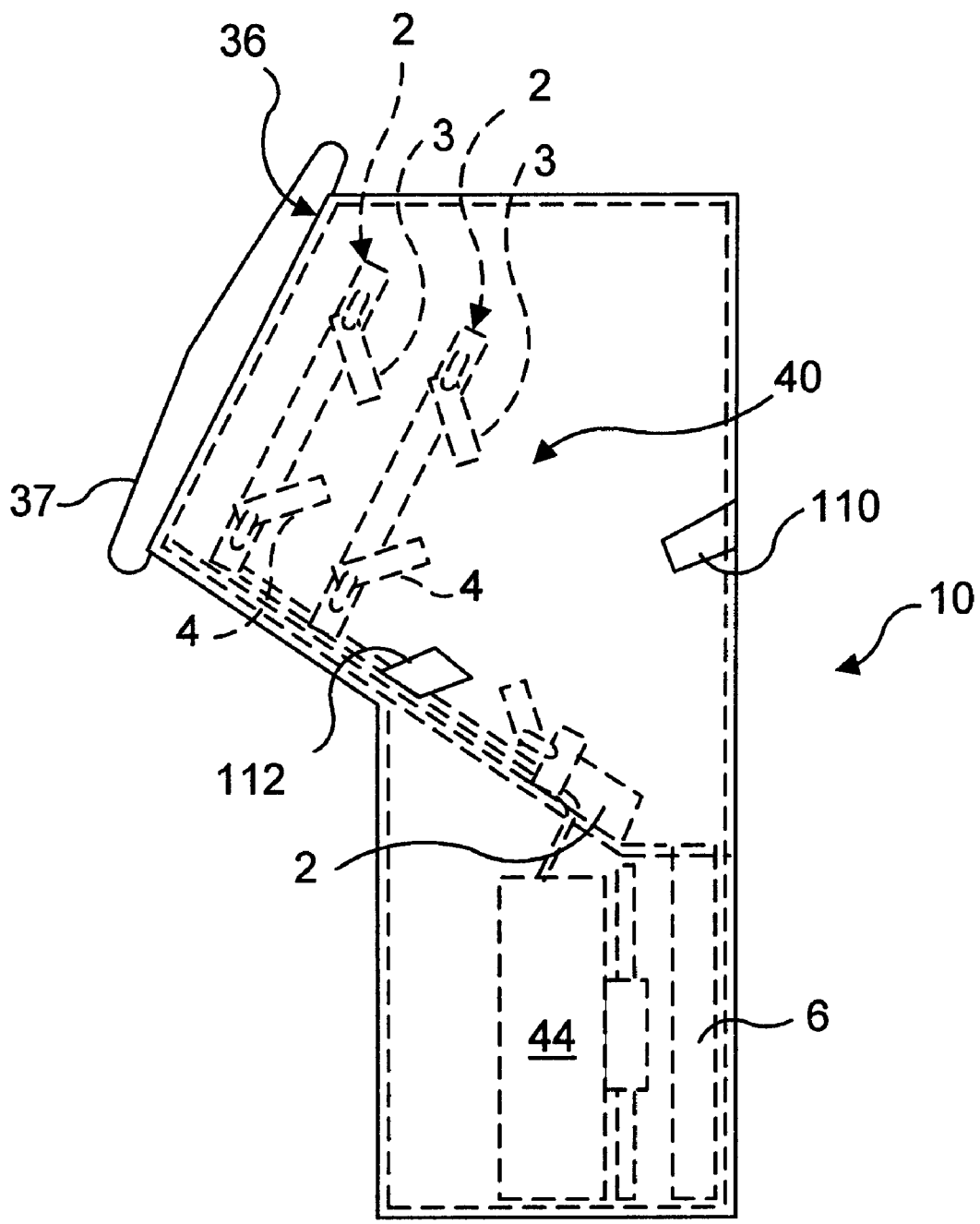
F I G. 7

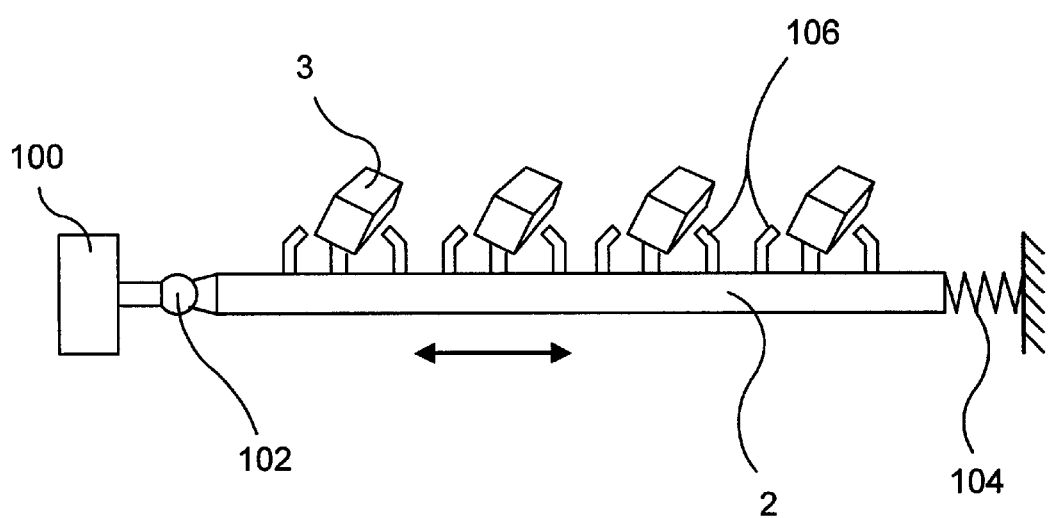
F I G. 9 ously minimizing the incidence of sepsis, infection, and disease. Until the 20th century the majority of war dead could be attributed to lack of sanitation and infection of, often, non-critical wounds; and, even during the Vietnam Conflict, death rates of 50 to 100 percent of the wounded were not uncommon. The tropical climate engendered significant pathogenic activity.

OSCILLATING LIQUID JET WASHING SYSTEM

BACKGROUND OF THE INVENTION

1. Field of the Invention

The invention relates to methods and apparatus for washing, cleansing and lavage utilizing pressurized oscillating liquid jets to remove particles, liquids, gels, oils, fats and microbial organisms from objects.

2. Brief Description of Related Art

The cleansing of objects, the washing of skin and the lavage of wounds has been the object of numerous inventions in the past. The cleansing of objects, in particular as it relates to the washing of human and animal body parts and skin for the purpose of reducing pathogens that may be transmitted to other objects or parties, is of critical interest to the medical, surgical and food handling communities. The ability to remove pathogens such as, for example, both transient *Escherichia coli* (*E. coli*), Salmonella and resident *Staphylococcus aureus* pathogens is critical to the minimization of the transmittal of such bacteria. Transient microorganisms are generally found on the surface of the skin and are picked up by handling of raw meats and from previously contaminated surfaces and are generally readily washed off by any number of washing techniques. The resident microorganisms found embedded in the pores and folds of the skin and tissues generally cannot be readily removed. *S. aureus* is found on over 30-percent of adult humans (Miller et al. "A Field Study Evaluating the Effectiveness of Different hand Soaps and Sanitizers," Dairy, Food and Environmental Sanitation, Vol.14, No.3, March 1994). Fast food establishments are particularly prone to passing on such pathogens merely because large quantities of food are handled and served to the public and because of the lack of adequate training and education in hygiene required of food handling personnel. While incidents such as the recent *E. Coli* outbreak in hamburger meat are relatively rare, they are nonetheless significant due to the large percentage of deaths attributed thereto. Even more significant, albeit far less publicized, is the large number of deaths occurring from hepatitis B in Pacific rim countries due to ingestion of contaminated sushi and raw meat that have been infected by food handlers to whom personal hygiene and cleanliness is not part of social customs or mores.

The critical care of injured or wounded personnel relies to a great extent on the degree to which pathogens, and non-pathogens which can become pathogenic in the wound environment, can be eliminated from wounds prior to their being operated on, consequently minimizing the incidence of sepsis, infection, and disease. Until the 20th century the majority of war dead could be attributed to lack of sanitation and infection of, often, non-critical wounds; and, even during the Vietnam Conflict, death rates of 50 to 100 percent of the wounded were not uncommon. The tropical climate engendered significant pathogenic activity.

Conventional scrubbing of skin, for example with cloths or brushes and soaps (both ordinary and antibacterial), is only moderately effective when a short procedure, such as is normally employed by marginally dedicated people, is used. Typically, about 50 percent removal occurs (Miller et al.). Surgical scrubs, which may last as long as 5–15 minutes, depending on the diligence and experience of the personnel, may remove as much as 90–91 percent of the transient micro-organisms, but very few, if any, of the resident microorganisms. A major problem with frequent scrubbing is the "dish-pan-hands" syndrome, redness, irritation and epidermal loss, which is associated with abrasion as well as increased sensitivity to chemicals when they are forcibly scrubbed on the skin. With present-day concerns about costs and efficiency, particularly with managed health care, time consumed in thorough hand washing becomes a major cost driver. When a 15 minute scrub is required even before a short procedure, this can limit the number of procedures that can be conducted during any given day.

It is well known in the art that pressurized liquids can be used to wash away materials and that, in combination with appropriate surfactants, detergents, soaps and anti-bacterial chemicals, the effectiveness of the removal of pathogens can be enhanced. By providing sweeping action to the pressurized jet stream, large areas can be washed and the angle at which the pressurized liquid jet impinges on a surface can be changed to provide an increased force on surface objects and particles to push them off the surface to which they adhere.

Pulsing the liquid is also taught in the art where the impulse forces of the liquid stream acting against particles helps to dislodge them. The oral irrigator is a good example of the use of a pulsating jet of water to help remove plaque from teeth. A major disadvantage of the pulsating irrigator is, however, that the high pressure axial pulses of liquid often tend to force bacteria and pathogens further under the gums, thereby actually promoting infection by introducing the bacteria directly into the blood stream.

Pulsating jets of water have also been adapted to presurgical cleansing of skin on the hands and forearms, and a particularly important effect is taught by Bhaskar et al. (U.S. Pat. No. 3,757,806) in their Pulsating Hydrojet Lavage Device, and by Decker et al. "A Rapid Method for the Presurgical Cleansing of Hands," Obstetrics and Gynecology, Vol. 51, No. 1, January 1978, wherein a plurality of nozzles located circumferentially and in depth in such a way as to provide coverage of a human hand and forearm, provide pulsating jets which pulse at a frequency that is in resonance with the dynamic response of the human epidermis, about 20–25 Hz, thereby causing the skin to resonantly vibrate wherein the pores, ridges and crevices of the skin alternately expand and contract in such a way as to loosen resident pathogens, such as *Staphylococcus aureus*, as well as embedded oils, greases, and dirt/solid particles. High pressure (50–80 psi) water jets flush the loosened matter away while depositing antibacterial chemicals as desired. Even when the device is operated at a frequency well above that of the skin resonance, 85 Hz, Bhaskar et al. show that their device provides comparable, if not better, bacteria removal in 90 seconds than a 10 minute surgical scrub. However, the same deleterious effect of embedding bacteria by the axial pulses may occur, albeit not to the same extent as in the oral irrigator.

Similar pulsating stream effectiveness is described in the lavage and debridement of wounds by Gross et al. ("The Effect of Pulsating Water Jet Lavage on Experimental Contaminated Wounds," J. Oral Surgery, Vol.29, March 1971) where a significant reduction in post-operative infections in test rats was observed.

Stouffer and Bauer (U.S. Pat. No. 3,973,558) with their swept jet oral irrigator teach that a similar resonant effect can be achieved on human gum tissue by sweeping a high pressure jet at the resonant frequency of gum tissue. Also by sweeping the jet over a substantial angle, up to about 90°, their device can provide for greater areal coverage thereby reducing the time required to effect cleansing. By using a fluidic oscillator they oscillate the fluid jet itself rather than the jet-issuing body thereby eliminating the need for costly and unreliable mechanically moving parts.

Despite the above teachings, currently commercially available hand washing systems, as exemplified and described in U.S. Pat. Nos. 3,699,984; 3,918,987; 4,219,367; 4,402,331; 4,817,651; 4,925,495; and 5,193,563, have not taken advantage of them. Typical of these devices is the invention of Crisp et al. Hand and Forearm Cleansing Apparatus, which shows a complex mechanical arrangement of rotating cylinders with spray nozzles therein, which only provide rotating steady jets of water to provide for good areal coverage but not in a manner as to stimulate any skin resonance effects. All of the above cited devices require electrical power, which is in itself dangerous in the wet environment, to operate a myriad of mechanically moving parts including pumps and rotating jet issuing bodies. The mechanical complexity of these systems results in a high cost which makes such systems unattractive to fast food establishments which operate on a very slim profit margin. While the cost of these systems would not be prohibitive in medical applications, the bulk, complexity, noise, and questionable reliability makes them unattractive for operating room use.

Sweeping jets without use of electricity or mechanically moving parts by using fluidic oscillation means is known in the art, the Stauffer et al. swept jet oral irrigator device, and the Bray (U.S. Pat. No. 4,463,904) windshield washer spray nozzle, being exemplary thereof. However, within the art of fluidic oscillators there are those that have different attributes and some are more suited to cleansing than others. The Stauffer et al. and Bray oscillators, while providing an oscillating jet, do so with relatively long dwell at the extremes of the jet spray so that there is little effectiveness in the middle of the fan spray. For gum massage and flushing this is not a detriment but for washing of large areas of skin this would require large, controlled, repetitive motion and reorientation of the hands and forearms to ensure proper coverage. Lack of proper repeatability could result in less than optimal results and the requirement for appropriate training in the use of such a system would make constant supervision necessary and somewhat unreliable. Uniform spray coverage with a fluidic oscillator is taught in the art by Bauer (U.S. Pat. No. 4,231,519 and U.S. Pat. No. Re. 33,159). Indeed, Bauer teaches the art of adjusting spray angle as well as uniformity. Frequency of the oscillating jet, as well as droplet breakup characteristics, are adjusted by the overall size of the device and the supply pressure of the liquid. Making the device larger reduces frequency and the frequency increases as the square root of the supply pressure (linearly with the fluid velocity).

SUMMARY OF THE INVENTION

Therefore, in light of the above, and for other reasons that will become clear when the invention is fully described, one object of the present invention is to provide an improved means of cleansing, washing or lavage with the attendant removal of bacteria, micro-organisms and pathogens without the use of any electrical, electronic or mechanical means at a cost that would make the system affordable and cost effective for food handling and pre-surgical operations of all types, thereby permitting widespread use.

It is another object of our invention to accomplish the aforementioned cleansing solely by the use of existing normal line water pressure for all operating power, without use of electricity to power any mechanical elements thereof.

It is a further object of this invention to provide an improved method and apparatus capable of automatically wetting, soaping and rinsing for specified times, but generally over a period of less than 90 seconds.

Yet a further object of this invention is to provide an improved means of providing a pulsating fluid stream for washing which is in resonance with the dynamics of the surface that is to be cleaned, the means for which is a fluidic oscillator which provides a lateral, as opposed to axial, pulsation on the surface, the laterally sweeping motion of which thereby increases the flushing/rinsing effectiveness of material removal and avoids the problem of further embedding materials and bacteria into subcutaneous tissues.

It is yet a further object of this invention, that the fluidic system operate with a minimum of moving mechanical parts, so that the entire washing process itself can operate with a minimum of maintenance. The timing, distribution and valving of the various fluids, water, soap, disinfectants, etc., may be accomplished fluidically; as a matter of practical consideration these functions may also be provided by highly reliable, low cost spool and shuttle flow- or pressure-operated valves. In keeping with the spirit of not using electricity because of its inherent danger, very low power, battery-operated electrical components, such as timers and use-compliance registration systems may be used outside of the fluid path without compromising safety, reliability or cost.

It is still a further object of this invention to provide a plurality of utilization modes ranging from permanent installations in operating rooms or restaurants to portable devices that can be used on a sink top in residences or temporary situations. In addition, the elements used together in different arays can be used in other sanitizing applications; washing of food stuffs, etc.

It is another object of this invention to provide for means of cleansing, washing or lavage in places where line water pressure, or adequate water pressure, is not available by allowing for a separate water pump.

Other objects of the invention will be apparent to those skilled in the art after a reading of the following description of the invention.

To explain the operation of the present invention, as well as to provide a basis for what is claimed, the following definitions, descriptions and descriptive figures are offered. While these descriptions go into specific details of the invention, it should be understood that variations may and do exist and will be apparent to those skilled in the art once they have read the descriptions herein.

In order to minimize any misunderstandings relative to the terminology used throughout this specification we wish to define the terms "cleansing" or "cleansing of micro-organisms" as being the substantive reduction in the total number of particles, bacteria, pathogens and/or micro-organisms on a given surface. Those skilled in the art will appreciate that absolute sterility is not achievable in most instances. In most circumstances bacterial and fungal populations are "cleansed" if reduced to levels acceptable for the particular circumstances.

Furthermore we define the term "epidermis" as being the generally accepted term describing the outermost layer of the skin organ, i.e., the layer devoid of blood vessels.

We wish to define the term "fluidic" in its specific description of fluid handling or control means "without" the use of mechanically moving parts.

We have interchangeably used the terms bacteria, micro-organisms and pathogens. While there is an accepted commonality between these terms, we wish to imply that when relating to deadly or disease transmission effects we are referring to pathogens, of which bacteria of course can be related to. A variety flora which may include spores and fungi, are included in references to micro-organisms a term which we have chosen to use to describe any microscopic living matter that can be found on or near the surfaces that are to be cleansed.

The term "particles" may refer interchangeably to solid or liquid matter or combinations thereof, such as fats, oils and grease, in small sizes such as droplets, dust, powders and any variety of organic or inorganic dirt and the like.

BRIEF DESCRIPTION OF THE DRAWINGS

FIG. 7 is a view along section 7—7 of the embodiment of FIG. 6 showing the internal configuration thereof.

FIG. 9 is a view of another embodiment fluid circuit, where the oscillator pivots along an arc.

DETAILED DESCRIPTION OF THE PREFERRED EMBODIMENTS OF THE INVENTION

Figure 1:
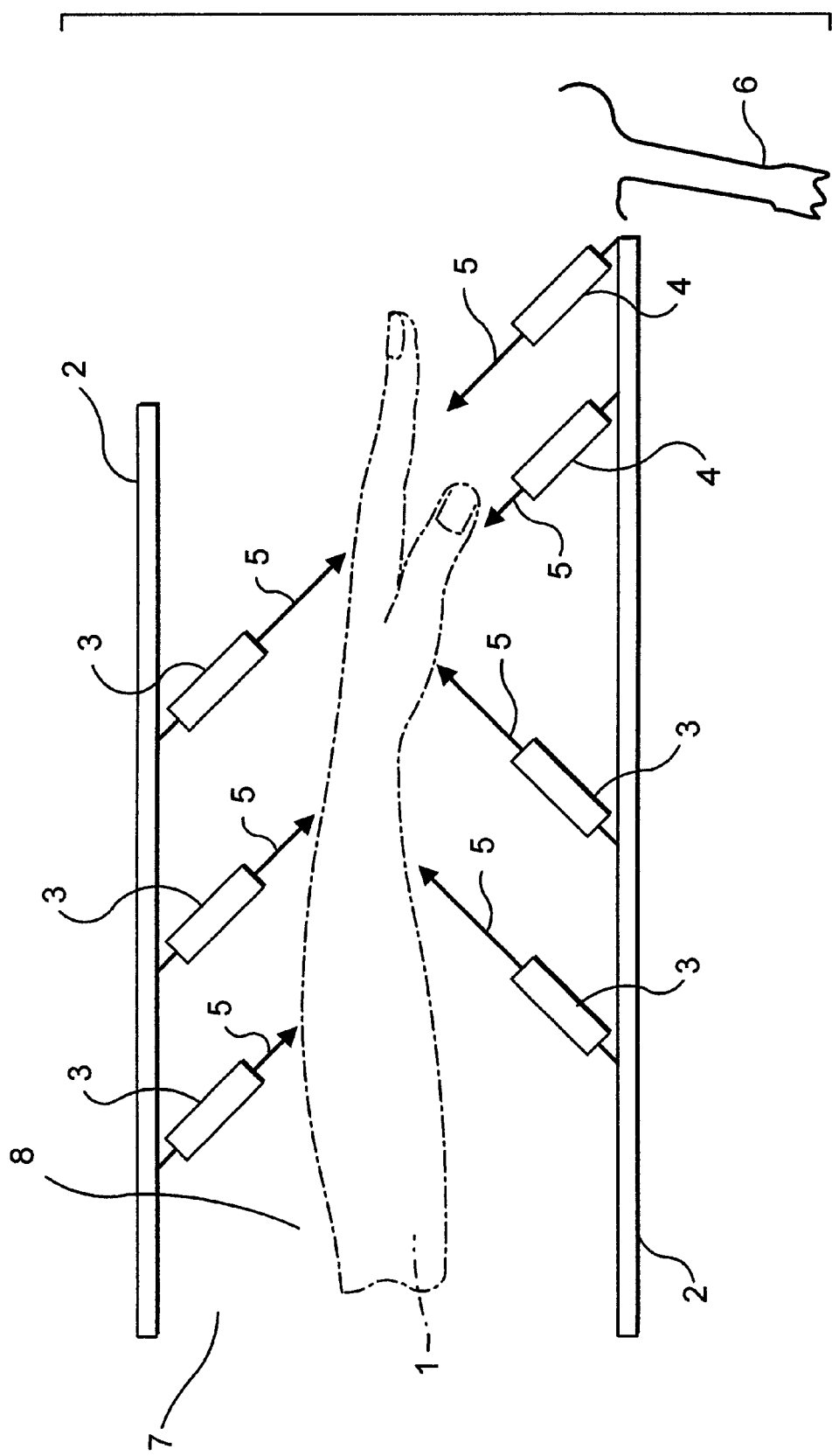
FIG. 1 is a notional lateral cross-sectional view of a hand and forearm inserted into embodiment cleansing apparatus showing spray patterns and arrangements.

The following detailed explanations of FIGS. 1–9 and of the preferred embodiments, when read by those skilled in the art, will reveal the method and apparatus of our invention. Although the following description is primarily concerned with "hand and forearm" washing of human limbs, it will be appreciated that the invention is not limited to the preferred embodiment but is applicable to any epidermal sites, including, but not limited to, proposed surgical sites. In addition, we wish to not be limited to human epidermal areas, but recognize that cleansing of the skin or surface of a variety of living or non-living beings including fish, poultry, mammals, vegetables, food stuffs, and the like is possible with our invention. Furthermore, we do not wish to be limited to epidermal layers, but also recognize that any pliant, porous or non-porous, surfaces that have resonant vibratory characteristics will benefit from cleansing using our invention. Such surfaces are exemplified by leather, upholstery, plastics and rubbers. We do not even wish to be limited by compliant surfaces, as we recognize that stiff or rigid surfaces and objects could be cleansed using our apparatus.

The method and process of the present invention comprises directing a plurality of laterally oscillating jets of a given liquid onto a selected area of skin to be cleansed in a predetermined manner in such a way as to effect cleansing of said skin. In the preferred method a number of different liquids are applied serially during the period of the cleansing cycle. Clean warm water is applied first whereby it wets the skin surface and removes large surface particles and moistens and softens the skin and warms any fats, oils and/or greases to reduce their viscosity or to fluidize them to such an extent that makes them more readily removed. The second liquid may be an aqueous antibacterial soap or disinfecting solution which by its surfactant action removes said oils, fats and greases, and by its sweeping or pulsatile action detaches micro-organisms from both the surface and the pores and folds. The third liquid may be plain water or may be a solution of water and emollients which rinse the skin, flush away the microorganisms, particles, fats, etc. and the dirty soap or disinfecting solution. The emollient ingredient is used to condition the skin to prevent chapping or to facilitate putting on surgical gloves and the like.

Those skilled in the art will appreciate that wash and rinse cycles may also apply other solutions, such as alcohols and the like to further reduce bacteria and other contaminants. Optional devices, not specifically associated with the cleansing mechanism, will provide cues to the user as to the nature of the on-going process, for example, one annunciator may signal the wetting cycle, another the wash cycle, yet another the rinse cycle, and finally another may signal when the hands may be removed signalling the end of the process. In the preferred implementation these annunciators, in keeping with our desire to not have any electrical/electronic principal elements, are water pressure activated and may be of the "winking eye" rotating colored ball type. Other optional devices attached to the apparatus may record statistics regarding the usage of the device, such as name or identifying number of the person using the apparatus, date and time of usage, total number of uses, and expendables remaining. These, of necessity are electronic, but are very low voltage battery powered devices.

Figure 2:
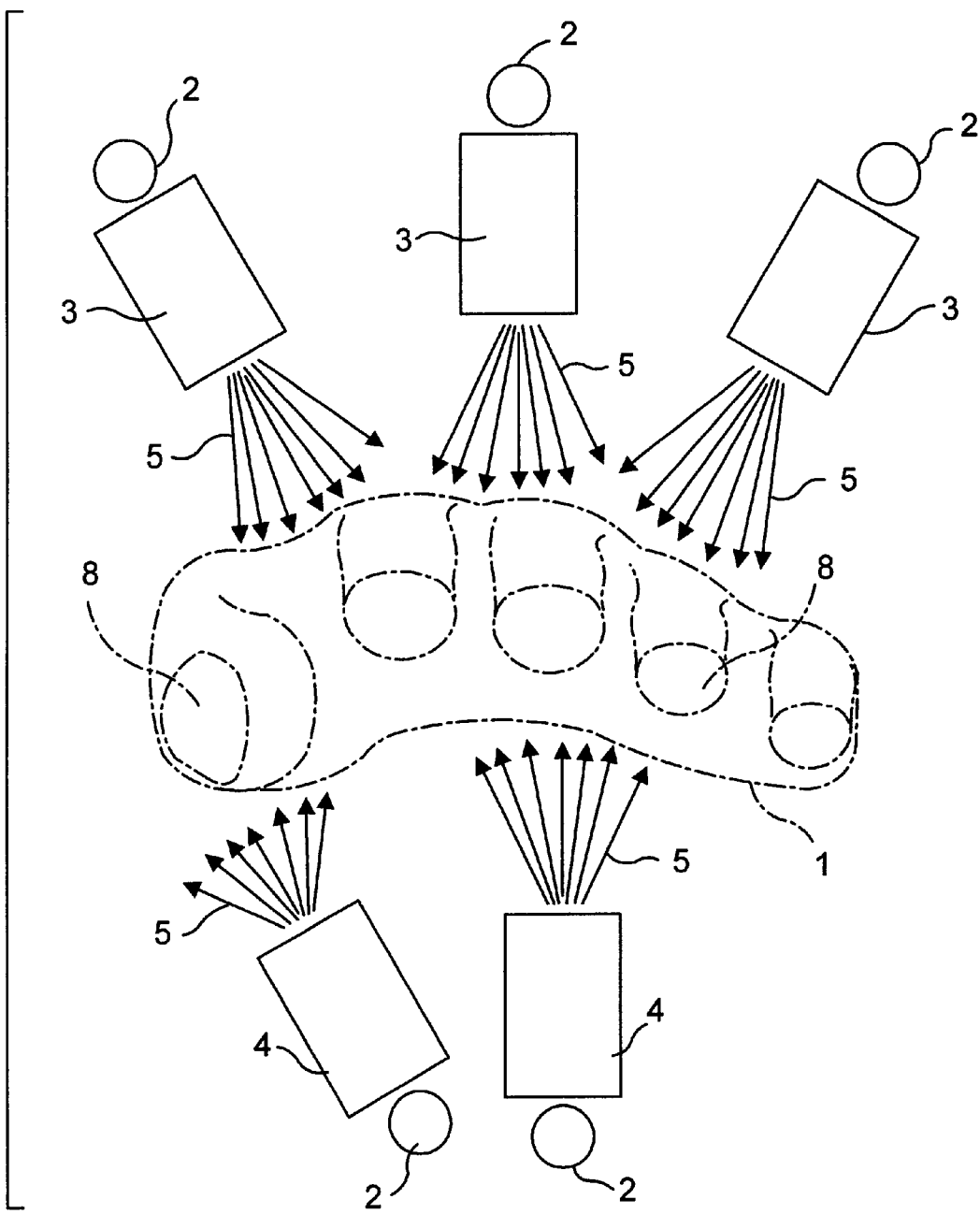
FIG. 2 is an axial cross-sectional view of a hand and forearm inserted into the cleansing apparatus of FIG. 1 showing spray patterns and arrangements with particular emphasis on the location of the spray nozzles for cleansing under the fingernails.
Figure 4:
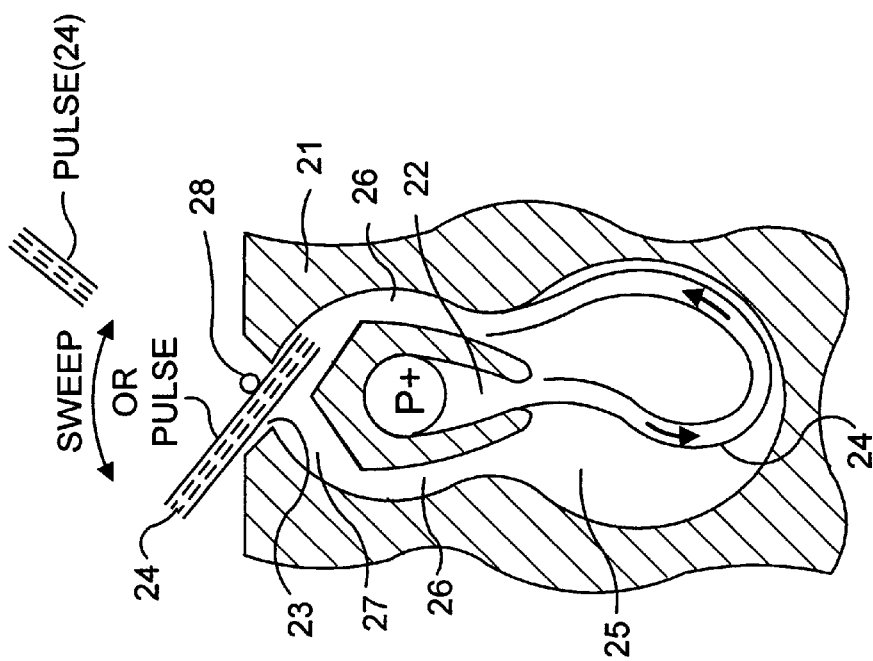
FIG. 4 schematically depicts, as in FIG. 3, the operation of a prior art Bauer fluidic swept jet oscillator that is used in the present invention.

FIGS. 1 and 2 are notional views of an embodiment of the cleansing apparatus showing, in general, the operation thereof. Referring to FIG. 1, the limb (hand and forearm) 1 is inserted through aperture 7 into a space 8 in which sweeping jet fluidic oscillators 3 and 4 are situated and which are connected to a source of liquid via the manifold 2. Liquid under pressure in the manifolds 2, is ejected through the plurality of oscillators 3, aimed at an angle away from the person's body to minimize undesirable splashback, and oscillators 4 aimed upward to clean under the fingernails. The oscillating sprays of liquid 5 impinge on the inserted limb 1 thereby cleansing it. Limb 1 may be moved slightly axially back and forth and the fingers flexed downward and outward to increase coverage and to enhance the pleasurable massage effect. Drain 6, a large orifice situated at the lowest point of the space 8, collects the liquid and passes it to a sewer or other appropriate drainage system (not shown in FIGS. 1 and 2). Referring now to FIG. 2 the laterally sweeping oscillating jets set up fan-shaped sprays 5 which massage the skin and at the same time set up the resonant vibration of the skin. The preferred frequency of oscillation to cause the skin of an adult human to resonate and thereby enhance the cleansing process of resident pathogens is between 20 and 80 Hz.

Fluidic oscillators 3,4 are mounted on manifolds 2 either in a fixed position or preferably pivotable on an arc of about 90 to 180 degrees. In a preferred embodiment as shown in FIG. 9, a view of one manifold 2, the oscillator 3 is mounted thereon on a pivot thereby allowing it to be positioned in any desired direction on a pre-determined arc. The manifold 2 functions in the manner of a cam rod to move laterally back and forth, as shown by the arrows, powered by a water motor 100 through a cam 102. Spring 104 aids return of the manifold 2 to its initial position. A stop 106 functions to cause the oscillator 3 to pivot on an arc as the manifold 2 moves laterally. This added mechanical motion of the oscillator 3 helps direct the pulsatile flow to further dislodge microorganisms, particles, etc.

Figure 3:
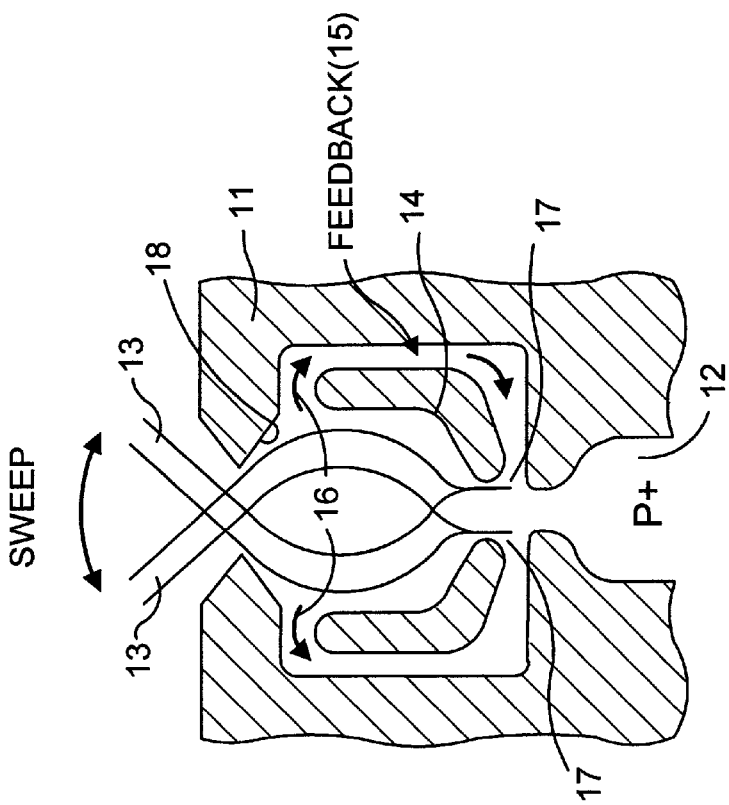
FIG. 3 schematically depicts the operation of a prior art sweeping jet fluidic oscillator.

Known art sweeping jet fluidic oscillators 3,4 are typified by the fluidic windshield washer spray nozzle shown in FIG. 3 which is exemplary of the Bray device (U.S. Pat. No. 4,463,904 incorporated herein by reference thereto). The oscillator 11 is comprised of a contracting nozzle 12 which accelerates the liquid to form a jet 13. Reduced pressure in the vicinity of the containing walls 14 preferentially attracts the jet 13 to one side or the other depending on the random occurrence of some small disturbances or turbulent eddies at the side of jet 13. The jet then is attracted to one wall by the well-known Coanda Effect. Once the jet is deflected to one side or the other flow will preferentially be fed into the feedback passage 15 and will traverse the passage in a time in accordance with the inertance of the feedback passage. This time combined with the time it takes for a fluid element to traverse the distance from the nozzle 12 to the inlet to the feedback passage 16 constitutes one-half of the oscillation period. That is, when the fluid interacts with the jet at the control nozzle 17 it will deflect the jet to the opposite side, thereby starting the second half of the oscillation cycle. The jet is turned by the wall 18 downstream of the inlet to the feedback passage and directed through an outlet nozzle or orifice and at the same time keeps the interior of the oscillator constantly filled with liquid, not allowing air to enter which would cause undesirable sputtering. These prior art feedback-type oscillators tend to have a non-uniform spray pattern in that the jet tends to dwell at the extremes of its deflection. The frequency of these devices can be modified by changing the overall dimensions and by altering the length and cross-sectional area of the feedback passage. Typical nozzle width dimensions of one of these oscillators is given by Bray to be 0.057-in and results in an oscillation frequency of several hundred hertz at pressures of 60 psi. To reduce the frequency by a factor of 10 would require increasing the dimensions ten-fold to an unacceptable size of over one-half inch. This is unacceptable because of the huge flow consumption that would occur as well as the unwieldy overall size of 6–8 inches. Size may be reduced by significantly increasing the feedback passage length, but since the primary feedback time is governed by the speed of sound, the length that would provide an appreciable increase in the oscillator time constant would be unacceptably long.

Figure 5:
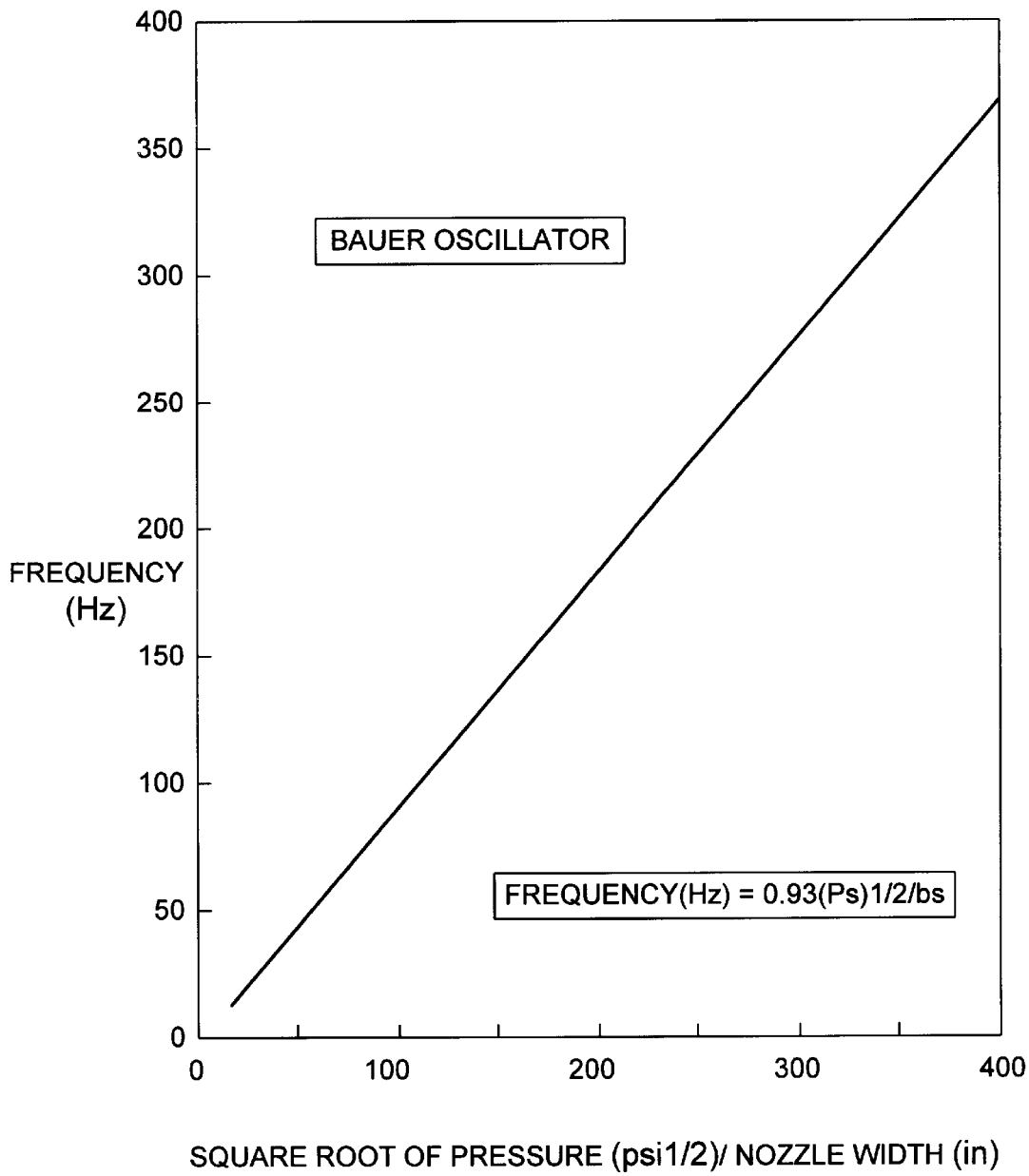
FIG. 5 graphically shows the relationship between the operating frequency of the prior art Bauer oscillator and the supply pressure and the device size as characterized by the nozzle width.

The preferred oscillator 3,4 configuration is the Bauer oscillator (U.S. Pat. No. 4,231,519 and U.S. Pat. No. Re. 33,159), both references incorporated herein in their entirety by reference thereto, shown in FIG. 4 which has significantly more flexibility to overcome the disadvantages of the typical feedback-type devices. The oscillator 21 incorporates a nozzle 22 which is, unlike in the conventional oscillator, oriented 180° away from the outlet orifice 23. A fluid jet 24 is formed and impinges on the end of the oscillator cavity 25 and is turned to flow up through the reactive passages 26. By turning the flow the flow must travel twice the distance of the length of the oscillator cavity 25. Thus, with a device of the same length as a conventional oscillator the transit time is twice as long thereby producing a lower frequency device of similar dimensions. Furthermore, the turning chamber 27 forms a fluid compliance which can be adjusted to interact with the inertance of the passages to produce a long L-C time constant which can be significantly greater than the acoustic propagation time. By introducing a blocking pin 28 in the outlet orifice the recovery pressure (outlet jet velocity) can be increased and the resultant twin jets can overlap to produce an extremely uniform pattern, albeit over a reduced fan angle. In the preferred implementation the nozzle width is 0.065-in, depth is 0.10-in, with an overall length of about 1-in. Depending on the relative length of the oscillator cavity 25 and the supply pressure, frequencies of from 20 to 80 Hz are achievable. FIG. 5 shows the relationship between frequency, supply pressure and oscillator nozzle width for the preferred embodiment. Of particular importance is the fact that the low skin and tissue resonance frequencies are achieved, and that it is clear that by only small increases of size (at the cost of a corresponding increase in flow consumption) even lower frequencies may be achieved or the same frequencies may be achieved at higher pressures.

Figure 6:
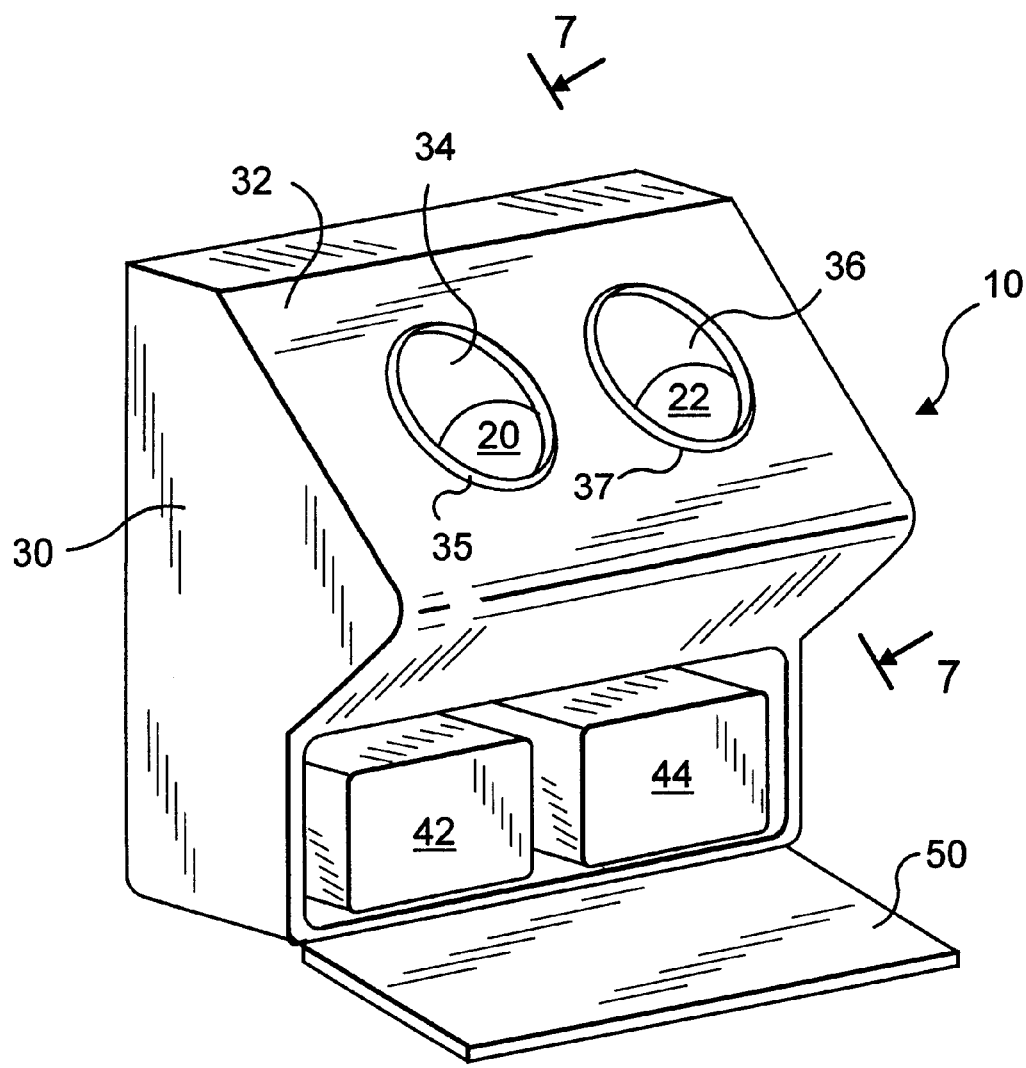
FIG. 6 is a front view of one embodiment of our apparatus useful in hand washing for food handlers and other employees of fast food establishments.

FIG. 6 is a view in perspective of one embodiment of our hand-washing apparatus useful, for example, to serve the needs of food handling workers and the like.

As shown in FIG. 6, a compact housing 30 defines the outside of a hand-washing apparatus 10 designed to be wall mounted. The housing 30 may be fabricated from any convenient material, preferably molded from a synthetic polymeric resin such as polyvinyl chloride, polyurethane, polycarbonate, polyethylene and like resins. The front panel 32 of the housing 30 bears two apertures 34 and 36 of a size and dimension to receive the hand, wrist and portion of a human forearm. The apertures 34 and 36 give entry to wash chambers 38,40 respectively. Apertures 34,36 are rimmed with a fluid-inflatable cuff 35,37 connected to a water supply line (not shown in FIG. 6). When a limb is inserted through the apertures 34,36 into chambers 38,40 and the wash cycle initiated, the cuffs 35,37 are inflated with water to form a loose seal with the inserted limb. This helps to inhibit splashing of wash liquids out of the apparatus 10. Cuffs 35, 37 deflate at end of wash cycle to permit removal of hands and forearms without further contact thus avoiding contamination from the cuff. The wash chambers 38,40 are lined with a plurality of fluidic oscillator spray oscillators 3,4 each of which directs an oscillating jet sprays into the chambers 38,40 at an oblique angle to epidermal surfaces of hands, wrists and forearms inserted into the chambers 38,40 through apertures 34, 36 respectively. As shown in FIGS. 1 and 2, the chambers 38,40 are adapted by size and configuration to roughly but closely contain inserted hands, forearms, etc. of an individual for washing. Those skilled in the art will appreciate that chambers 38,40 can be modified in size and configuration to contain and surround for washing the article to be washed such as other parts of human anatomy, including the torso and other limbs, poultry, devices, other animals and articles as previously described. Compartments 42 and 44 house circuits for supplying water and cleansing solutions to oscillators 3,4 as will be described hereinafter. FIG. 7 is a cross-sectional side elevation in-part along lines 7—7 of FIG. 6 enlarged to show the plurality of arranged spray oscillators 3,4. A front panel 50 is shown opened in FIG. 6 to expose the internal washing circuits 42,44 and components which supply the chambers 38,40 with wash or cleansing solutions for operation of the apparatus 10.

Figure 8:
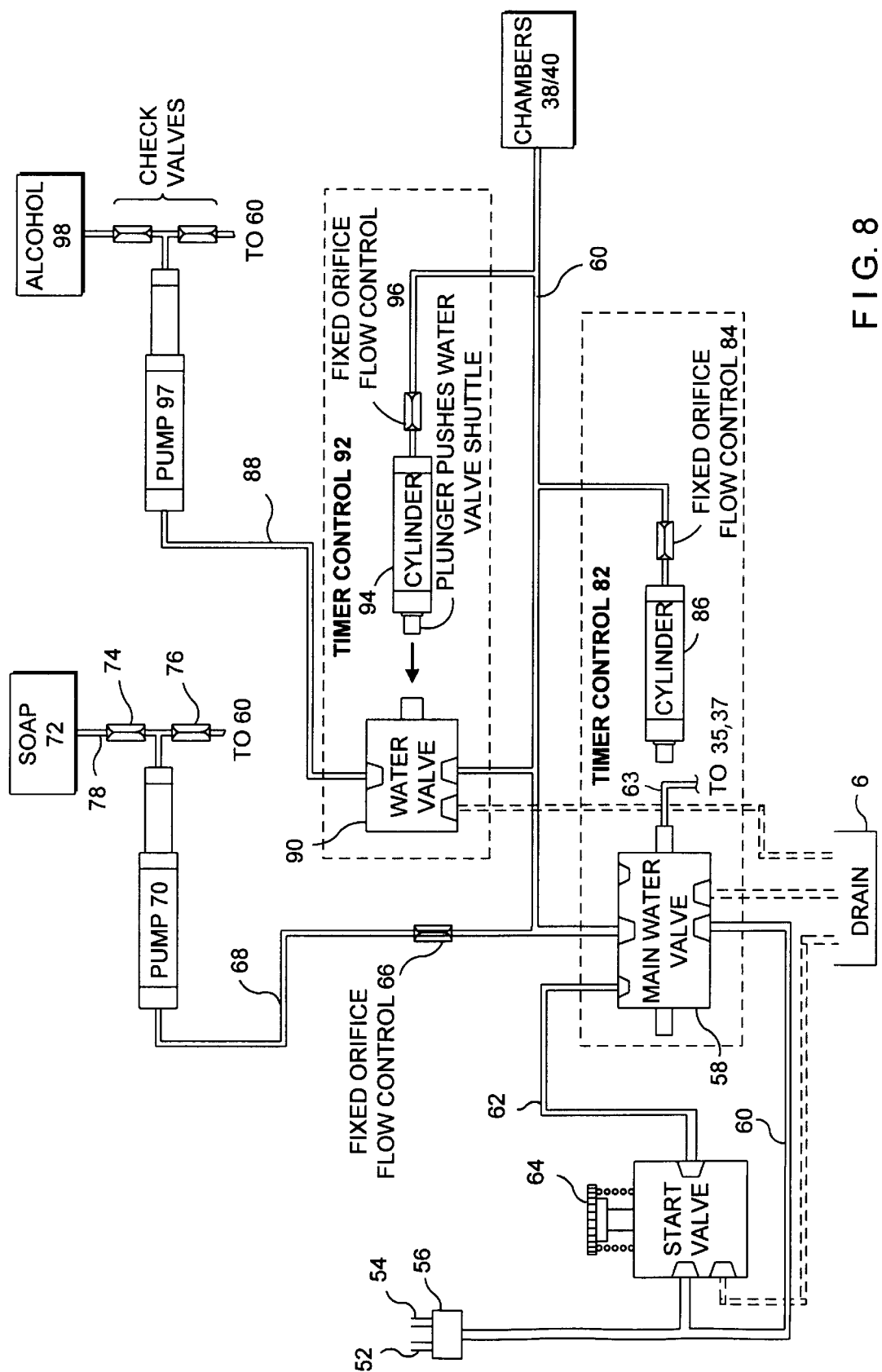
FIG. 8 is a schematic diagram of the fluid circuitry of one implementation of our invention showing the operational components and circuitry employed in the embodiment of FIG. 6.

FIG. 8 is a schematic drawing showing a representative wash circuit within housing 12 of the embodiment apparatus shown in FIG. 6. Water feed lines 52,54 supply hot and cold water respectively to a temperature controlled mixing flow valve 56 which mixes hot and cold water to permit output flow of water at a pre-determined constant temperature. Advantageously, water passing out of valve 56 is at a temperature within the range of from about 40° C. to 50° C.

Suitable mixing valves 56 are well known in the art and are described for example in U.S. Pat. No. 5,341,987 incorporated herein by reference thereto. Water at a pre-determined temperature is valved into the oscillators 3,4 within each scrubber chamber 38,40 through the agency of conduit line 60 at an advantageous water line pressure of 30 to 70 psi. Inserted in conduit 60 is a controlling main valve 58. In the preferred embodiment of FIG. 8, a pre-determined and measured quantity of water is delivered to the chambers 38,40 from valve 58 through a secondary circuit 62 which carries the water past a foot-controlled starting valve 64. Momentary actuation of start valve 64 will allow water into a pilot of main water valve 58 starting the scrub/wash cycle. A secondary flow of water from main valve 58 passes through conduit 63 to inflate the cuffs 35, 37. When main water valve 58 opens, water immediately is sent to chambers 38,40 through conduit 60 starting the wet-down cycle (preset time) then the water (a small portion) is released by main valve 58 past fixed orifice flow control valve 66 into conduit 68 leading to syringe pump 70. Syringe pump 70 receives a charge of soap solution from vessel 72 and starts the pump 70 cycle introducing soap into the chambers 38,40 through conduit 60 for a preset time.

Delivery of soap mix from syringe pump 70 to conduit 60 is controlled by control valves 74,76 in conduit 78. The main water valve 58 also starts a time cycle through the timer control 82 which introduces water through the fixed flow control 84 and into the cylinder 86 causing a preset delay before a final rinse or other solution such as alcohol or another final wash solution is pumped into the chambers 38,40. (This occurs during the last few seconds of the cycle. As shown in the preferred circuit of FIG. 8, a secondary water conduit 88 branches off conduit 60 and is controlled by valve 90. Valve 90 through time delay mechanism 92 (cylinder 94 and fixed orifice flow control 96) provides a portion of water to syringe pump 97 for receiving a final rinse solution from vessel 98, mixing the solution with water and re-inserting the mix back into conduit 60 upon time control.

After the soap cycle time a water rinse cycle remains on for an additional preset time which will stop the complete cycle when the cylinder 94 in timer control 82 actuates the plunger in the water valve 90 to complete the wash cycle.

Water continues to flow through main valve 58 until the cycle has completely discharged, then main valve 58 will shut-off and remain closed until start valve 64 is again actuated. The time main valve 58 is open, depends on the setting of the flow control valves and the time it takes to discharge the cylinder 86. The soap pump 70 recharges when main valve 58 is shut off. In operation, then, actuating start valve 64 will allow water through fixed orifice flow control valve into the lower chamber of water timer accumulator 68 and also into the shift pilot of main water valve 58.

Start valve 64 is released starting the timing cycle and main water valve 58 sends water first to scrub wash chambers 38,40 and into water timers. The hydraulic circuitry of FIG. 8 is a simple design which obviates the need for electrical components or extensive plumbing. It is compact and easy to manufacture. Of course, those skilled in the art will appreciate that more sophisticated mechanisms with additional functions can be provided when so desired. For example, in an electronic control system a timer module can be connected to signal actuate the main valve 58 by a solenoid, thereby sending water to the oscillators 3,4 in chambers 38,40. The timer module can then signal the soap syringe pump 70 to discharge. After discharge, continued water flow provides a rinsing phase, and then when rinsing is completed the time module signals main valve 58 to close. Also, the circuit could be implemented with no-moving-parts fluidic elements at a small penalty of extra flow.

Those skilled in the art will appreciate that the embodiment of FIG. 8 is merely representative of cycles and wash fluids that may be employed in the apparatus 10 of the invention. For example, the fluids and wash cycles described in U.S. Pat. No. 4,925,495 may be used to modify the embodiment of FIG. 8. The U.S. Pat. No. 4,925,495 is hereby incorporated herein by reference thereto.

The FIG. 8 does not show electrical wiring between component parts, for clarity of the drawing. However, there may be hermetically sealed within the enclosure 30 a power source, for example, a long-life battery such as the conventional and well known nickel-cadmium or lithium batteries that provide about 1 to 1.5 volts. Mounted on a printed circuit board and powered by the power source may be an application-specific integrated circuit (ASIC) such as a logic array or a microprocessor programmed to process signals from a sensor and trigger a signalling device such as, for example, a visual indicator, for example a light emitting diode (LED) or a liquid crystal display (LCD) to give an alpha-numeric readout. LCD devices controlled by electronic signals from ASIC are well known and may be for example the type described in U.S. Pat. Nos. 4,804,953; 5,227,899; and 5,227,901. The ASIC is a control means and if it is more specifically a microprocessor it includes a suitable central processing unit (CPU) for operating the control functions of the ASIC. The ASIC can be a digital integrated circuit serving control functions including timing functions, memory recordings, visual and auditory indicators and reporting data to a printer. An optional random access memory (RAM) and/or programmed read only memory (PROM) means is connected to the ASIC. The memory means is associated with the ASIC so that a history of the number of actuations and by whom can be maintained, together with, for example the date and time of use, for analysis later. The RAM and/or PROM means can be a bubble memory, hysteresis memory or any known memory device. The hermetic sealing of the electronic components within enclosure 30 can be further protected by over-coating the entire assembled circuit within enclosure 30 with a waterproof resin, such as, for example, a polyimide resin or a parylene resin.

In conjunction with an LCD, the ASIC can be programmed to provide a liquid crystal display (LCD) giving time and date and the point of any wash cycle then occurring.

Other improvements to the basic circuit described above include connection to means for recording times and dates of use by individuals (identified by bar code indicia inserted into the apparatus of the invention to start a wash cycle).

In a preferred embodiment of the invention, an infra-red light emitter 110 is mounted in a hermetically sealed unit within each of the chambers 38,40 as shown in FIG. 7. Opposite the emitter 110 is an infra-red detector 112 positioned to receive radiation from the emitter 110. The emitter 110 and detector 112 are part of a closed circuit which, when interrupted by an inserted limb, activates the wash cycle. By connection of the circuit with a microprocessor, records and logs may be maintained for recording the completion of a wash cycle and the identity of the personnel who have used the apparatus 10. A solenoid can be inserted in the circuit to operate the main valve 58.

Where U.S. patents are referred to above, the contents of their disclosures are thereby incorporated herein by reference thereto.

Although the invention has been described above in terms of preferred embodiments for hand, wrist, and forearm washing and cleansing, those skilled in the art will appreciate that the scope of the invention is broader.

The following preparation and Examples show and describe the manner and process of carrying out the invention, but are not to be construed as limiting the scope of the invention.

Test Procedures for Establishing Efficacy of the Present Embodiment

1) Manual Wash (Control for Comparison).

Subject hands of a number of volunteers were selected based upon a randomizing technique. A selected hand was pressed (front and back) onto a plate of agar while the force of this application was monitored and controlled. This force was 3 to 5 pounds. The subject selected hand was then manually washed using a surgical scrub kit (brush). The manual wash was performed in a consistent manner for all subjects for 120 seconds. Water temperature was set at 40° C. and the pressure was adjusted appropriately and recorded. The process begins with a 20 second rinse followed by a 60 second manual scrub performed by the investigator. The manual wash procedure is completed with a 40 second rinse. The hand was hot-air dried using a hair dryer. A post wash culture was then taken as before.

2) Fluidic Handwasher

The hand opposite the one selected for the manual wash was utilized for the fluidic wash using the apparatus of FIG. 6. The selected unwashed hand was cultured by pressing (front or back) onto plate of agar while the force of this application was monitored and controlled. This force was 3 to 5 pounds. This provided a measure of the bacterial count prior to washing. The fluidic handwasher was readied by adjusting water temperature to 40°. The fluidic wash was performed in a consistent manner for all subjects for 60 seconds. This process consisted of 20 seconds of initial water rinse, followed by an automated wash using 40 ml of a 4-percent solution of chlorhexidine gluconate in a detergent base injected over a period of 30 seconds. The automated wash was completed following a 10 second water rinse. The hand was then dried with hot air from a hair dryer. A post wash culture was performed as before.

Handwasher Test Protocol

By definition the surgical hand brush scrub is intended to remove or destroy transient microorganisms and reduce resident flora. This condition can be detected by inoculating a growth media on a suitable plate by hand contact and subsequently counting the resulting incubated colony formation. It is widely held that the presence of transient microorganisms and resident flora can be significantly reduced by a combination of an appropriate cleansing agent and a vigorous manual wash. The objective of this experiment was to compare the efficacy of a handwash technique utilizing a fluidic oscillator nozzle as described above with that of an aggressive manual surgical scrub. In this study we held the quantity of cleansing agent constant by utilizing a 4-percent chlorhexidine gluconate in a detergent base. This type of cleansing agent is highly recommended by the Association for Professionals in Infection Control and Epidemiology, Inc. (APIC) Guideline for Handwashing and Hand Antisepsis in Health Care Settings.

As can be seen, the handwasher of this present invention can be as effective as manual surgical scrubbing of twice the duration, without the attendant effort and in less time.

Those skilled in the art will appreciate that the preferred embodiments described above may be used in a wide variety of applications, for example in:

---

HEALTHCARE

Hospital operating rooms
Burn patient wound debridement
Infusion/dialysis centers
Medical clinics
Dental offices
Institutional healthcare offices
Commercial and hospital laboratories
Nursing homes
Retirement community facilities
Daycare centers
Emergency Medical Service (EMS)
Military field hospitals
Military Decontamination (Field)

FOOD HANDLERS

| Fast food outlets | Meat and poultry packers |
| Restaurants | Supermarkets |
| School cafeterias | Hotels |
| food caterers | |
| Food handlers, processors, butchers | |

INDUSTRIAL

| Electronics assembly | Oil rigs |
| Industrial cleanrooms | Petroleum refineries |
| Chemical plants | Gasoline stations |
| Automotive and marine repair facilities | |

CONSUMERS

| Consumer households | Pet owners |
| Beauty salons | Highway rest stops |

VETERINARY

| Animal hospitals | Veterinarians |
| Veterinary schools | Pet grooming |

---

What is claimed is:

1. A process for cleansing a pliant surface of an object, including a human, of microorganisms which comprises;
   selecting an area of the pliant surface for cleansing;
   providing an oscillatory jet spray of a cleansing solution, said jet spray providing a lateral, as opposed to axial, pulsation on the surface, pulsation being in resonance with the dynamics of the pliant surface that is to be cleaned, the laterally sweeping motion of which thereby increases the flushing/rinsing effectiveness of material removal and avoids the problem of further embedding materials and bacteria into the surface; and
   directing the oscillatory jet spray upon the area for a time sufficient to achieve a desired degree of cleansing.

2. The process of claim 1 wherein the microorganism is *E. coli.*

3. The process of claim 1 wherein the object is a human.

4. The process of claim 3 wherein the area comprises the hands, wrists and a portion of the forearms of a human.

5. The process of claim 1 wherein the oscillatory jet spray is at a frequency similar to the resonant frequency of the surface.

6. The process of claim 5 wherein the frequency is in the range of 20 to 80 Hz.

7. The process of claim 1 wherein the solution is a soap solution.

8. The process of claim 1 wherein the solution comprises water.

9. The process of claim 1 wherein a plurality of different solutions are applied in a sequence of order.

10. The process of claim 9 wherein the sequence is timed.

11. Apparatus for cleansing microorganisms from surfaces which comprises:

means having at least one nozzle which accelerates a liquid to form a jet, means for supplying a fluidic stream for cleansing, under pressure of 30 to 70 psi at the nozzle without the use of electricity to power the supply, connected to means for laterally oscillating and spraying a pulsating fluidic stream;

means for laterally oscillating and spraying the pulsating fluidic stream said stream being comprised of different compositions for wetting, washing and rinsing operations, for effective cleansing of a selected area; means for controlling the time that the fluidic stream is oscillated and sprayed; and means for directing the fluidic stram on the surface as a spray for a time sufficient to achieve a desired degree of surface cleansing.

12. The apparatus of claim 11 wherein the microorganism is *E. coli.*

13. The apparatus of claim 11 wherein the surface is the epidermis of a human.

14. The apparatus of claim 13 wherein the epidermal surface comprises the hands, wrists and a portion of human forearms.

15. The apparatus of claim 11 where the oscillator means is a fluidic swept jet oscillator.

16. The apparatus of claim 15 where the oscillator operating frequency is chosen to be similar to the resonant frequency of the surface being cleansed.

17. The apparatus of claim 16 where the oscillator frequency is 20–80 Hz to correspond with the resonant characteristics of the human epidermis.

18. The apparatus of claim 11 where the wetting liquid is water.

19. The apparatus of claim 11 wherein the washing liquid is an antibacterial soap solution.

20. The apparatus of claim 11 where the rinsing liquid is water.

21. The apparatus of claim 11 wherein the means for controlling the time that the liquid is sprayed includes multiple timing means.

22. The apparatus of claim 21 wherein the timing means are hydraulically operated valves and accumulators.

23. The apparatus of claim 21 wherein the timing means are electronically controlled valves.

24. The apparatus of claim 23 wherein the electronic means is a microprocessor.

25. The apparatus of claim 24 wherein the microprocessor provides additional functions of recording the number of utilizations and a log of personnel using the handwasher.

26. The apparatus of claim 11 which further comprises annunciators to signal the wetting, cleansing and rinsing operations.

27. Apparatus for washing selected pliant surface areas, which comprises;

a swept jet fluidic oscillator spray head having at least one nozzle which accelerates the liquid to form a jet for supplying a fluidic, stream for cleansing, under pressure of 30 to 70 psi at the nozzle without the use of electricity to power; means for holding the nozzle at an angle oblique to the pliant surface area; and, conduit and control means connected to the fluidic oscillator for delivery of oscillating let spray of a cleansing solution to the pliant surface at an angle oblique to the pliant surface.

28. The apparatus of claim 27 wherein the selected surface areas are on the epidermis of a human.

29. The apparatus of claim 28 wherein the epidermal surface comprises the hands, wrists and a portion of human forearms.

30. The apparatus of claim 27 wherein the means for controlling the time that the liquid is sprayed includes multiple timing means.

31. The apparatus of claim 30 wherein the timing means are hydraulically operated valves and accumulators.

32. The apparatus of claim 30 wherein the timing means are electronically controlled valves.

33. The apparatus of claim 32 wherein the electronic means is a microprocessor.

34. The apparatus of claim 33 wherein the microprocessor provides additional functions of recording the number of utilizations and a log of personnel using the handwasher.

35. Apparatus for washing selected pliant surface areas, which comprises;

a swept jet fluidic oscillator spray head; means for holding the spray head at an angle oblique to the pliant surface area; and, conduit and control means connected to the fluidic oscillator for delivery of oscillating let spray of a cleansing solution to the pliant surface at an angle oblique to the pliant surface at a frequency which is set to coincide with the resonant frequency of human epidermis.

36. The apparatus of claim 35 wherein the resonant frequency is 20–80 Hz.

37. A process for cleansing microorganisms from a pliant epidermal surface of a human hand, which comprises;

brushlessly scrubbing the pliant epidermal surface of a human hand with a plurality of cleansing fluids sprayed in an ordered sequence, said fluids and sequence comprising;

(i) first spraying water for a period of at least about 20 seconds on the surface of the hand at an angle oblique to the surface axis;

(ii) second, spraying an aqueous solution of a detergent and a bactericide for a period of at least about 30 seconds on the surface at said angle; and (iii) third, spraying an aqueous rinse for at least about 10 seconds on the surface at said angle;

said first, second and third sprayings being fluidic sprays which are pulsating, laterally oscillating sprays at a frequency of from 20 to 80 Hz and a temperature of from 40 to 50° C.;

whereby a cleansing of the hand is obtained substantially equivalent to a surgical brush scrub of at least about 120 seconds at said temperature.

38. The process of claim 37 wherein the aqueous solution is a 4 percent solution of chlorhexidine gluconate in a detergent base.

39. The process of claim 37 wherein the spray impacts the surface at a force of 30 to 80 psi.

40. The process of claim 37 wherein the temperature is 40° C.

* * * * *